United States Patent [19]
Lawson et al.

[11] Patent Number: 4,755,461
[45] Date of Patent: Jul. 5, 1988

[54] TABLETED BLOOD PLASMA MICROCONCENTRATED THROMBOPLASTIN COAGULATION REAGENT

[75] Inventors: Daniel E. Lawson, Ambler; Eugene J. Messa, Doylestown; Michael Sokol, Melrose Park, all of Pa.

[73] Assignee: Bio/Data Corporation, Hatboro, Pa.

[21] Appl. No.: 853,084

[22] Filed: Apr. 17, 1986

[51] Int. Cl.$^4$ .............................................. C12Q 1/56
[52] U.S. Cl. ...................................... 435/13; 435/810; 436/18; 424/101
[58] Field of Search ...................... 435/13, 810; 436/18

[56] References Cited

U.S. PATENT DOCUMENTS

| | | |
|---|---|---|
| 3,179,567 | 4/1965 | Owren . |
| 3,395,210 | 7/1968 | Lanahan et al. ................ 424/2 |
| 3,413,198 | 11/1968 | Deutsch ........................ 195/103.5 |
| 3,511,607 | 5/1970 | Green ............................ 23/230 |
| 3,980,432 | 9/1976 | Trobisch et al. . |
| 3,983,004 | 9/1976 | Trobisch et al. . |
| 3,997,470 | 12/1976 | Monte et al. ................... 252/408 |
| 4,337,254 | 6/1982 | Moncada ........................ 424/251 |
| 4,416,812 | 11/1983 | Becker et al. ................... 435/13 |
| 4,458,015 | 7/1984 | Jering et al. .................... 435/13 |
| 4,477,437 | 10/1984 | Tamai et al. .................... 424/116 |

FOREIGN PATENT DOCUMENTS

| | | |
|---|---|---|
| 2316430 | 10/1975 | Fed. Rep. of Germany . |
| 2356493 | 9/1976 | Fed. Rep. of Germany . |
| 1017075 | 12/1952 | France . |
| 10113192 | 12/1965 | United Kingdom . |

Primary Examiner—Sam Rosen
Attorney, Agent, or Firm—Seidel, Gonda, Goldhammer & Abbott

[57] ABSTRACT

The invention herein is directed to an improved thromboplastin composition wherein the thromboplastin is supplied in a tablet separate from calcium salts in order to stabilize the thromboplastin.

21 Claims, No Drawings

4,755,461

TABLETED BLOOD PLASMA MICROCONCENTRATED THROMBOPLASTIN COAGULATION REAGENT

BACKGROUND OF THE INVENTION

This invention relates to an improved tableted blood plasma microconcentrated thromboplastin coagulation reagent and a method for making it.

The invention is an improvement over the concept of preparing tableted blood plasma microconcentrated coagulation reagents generally. While methods for preparing blood plasma coagulation reagents have been known, the preparation of the reagents in tableted form is a recent innovation. Diagnostic or monitoring coagulation reagents are not amenable to manufacture using standard routes of biochemistry or automated production line techniques for producing tablets. Coagulation materials are extremely sensitive to degradation or alteration through improper processing and storage. Further, by their very nature, starting materials for coagulation reagents are frequently not at the same level of chemical activity, re-activity, purity, and so on. This means that every process step has to be customized depending on the starting materials used in each case.

Even with tailoring of the starting materials to safeguard against uneven activity, reactivity, purity, and the like, additional precautions must be taken to prevent contamination and deactivation of the active materials. Carriers, disintegrating agents, fillers, binders, and other materials commonly used in preparing tablets can be the source of such contamination or deactivation. Consequently, the technology involved in tableting coagulation reagents had to depart significantly from pharmaceutical or therapeutic utilities which employ a very large percentage of inert materials in every capsule or tablet.

Taking every precaution and exercising the highest degree of care, one can still encounter difficulties in tableting diagnostic coagulation reagents. One problem that has arisen in the tableted thromboplastin coagulation reagent appears to derive from a possible incompatibility between calcium and thromboplastin, both of which are critical to the performance of the coagulation test.

In preparing tableted thromboplastin coagulation reagents, problems arose in metering granules of the components to achieve accurate ratios of calcium and thromboplastin. Beyond that, and apparently because of the incompatibility of the two materials, some difficulty has been experienced in producing consistently homogeneous tablets at commercially acceptable yields, even from a homogeneous mixture of thromboplastin and a calcium salt. Inhomogeniety could sometimes be observed from tablet to tablet as well as within a select tablet. The combined components did not maintain their respective ratios consistently enough during the tableting operation to justify full-scale commercialization.

Another problem that has been encountered derives from the fact that calcium salts such as calcium chloride act as desiccants. Even though the calcium chloride is imprisoned in a tablet and even though the tablet is encapsulated in air tight packaging, the calcium salt can absorb moisture into the tablet. Moisture causes aggregation of thromboplastin with calcium as well as with other colloidal thromboplastin particles. As a result, the thromboplastin aggregates or agglomerates fall out of solution and do not participate as required in the test procedure.

SUMMARY OF THE INVENTION

It has now been found that the problems encountered in tableting diagnostic thromboplastin coagulation reagents can be obviated when the thromboplastin is tableted with a buffer, binder, and lubricant in one tablet; and calcium lactate, calcium gluconate, or calcium chloride, hereinafter referred to as the calcium salt(s), is contained in another tablet. Calcium lactate and calcium gluconate are prefered since they can be tableted without using fillers or bulky materials that could introduce contamination, or deactivate, or otherwise interfere with the reagent. The tablets may also contain stabilizing agents, disintegrating agents, antimicrobial preservatives and other additives as desired and the calcium-containing tablet may also contain buffer, binder, and bulking agent if desired. The thromboplastin-containing tablet preferably contains an antimicrobial preservative in order to protect the thromboplastin if the reagent is not used immediately and preserve the stability of the reagent on storage. An antimicrobial preservative also helps to preserve reconstituted stability. Unexpectedly, the aggregation phenomenon heretofore observed does not occur when the calcium salt of this invention is tableted separately from the thromboplastin, even though the calcium containing tablet is packaged together with the thromboplastin containing tablet.

DETAILED DESCRIPTION OF THE INVENTION

The dual tableted thromboplastin reagent of this invention is particularly suitable for use in the Prothrombin Time (PT) test. One tablet contains the lyophilized phospholipid, thromboplastin, and the other tablet contains the calcium salt of the invention. The preparation of the thromboplastin reagent described herein is referenced to a manufacturing batch having a volume of one liter. Percentages are all by weight and are based on the weight of a one liter manufacturing batch. The molar quantities specified are those to be used for a one liter manufacturing batch. Percentages by weight given for a lyophilized material are based on the weight of lyophilized material derived from a one liter manufacturing batch. The size of the manufacturing batch can be varied with corresponding variation in the quantities of the components as specified herein.

In the following description, a thromboplastin microconcentrated reagent is formed by dry blending a binder and a lubricant with a lyophilized active ingredient or ingredients or buffer, or dry blending a lubricant with a lyophilized active ingredient or ingredients and binder to form a dry blend batch. In another method, a solution of the lyophilized active ingredient and binder is sprayed onto granules of lyophilized buffer to form a dry blend batch. The thromboplastin-containing tablet may also contain other materials provided only that the thromboplastin and calcium are contained in separate tablets. Two or more dry blend batches may also be combined to increase the size of the final manufacturing batch. The final dry blend batch is then compacted, granulated, and tableted. The calcium-containing tablet is formed by dry blending a calcium salt of this invention with a binder and a lubricant. If desired, the calcium-containing tablet may contain other materials provided only that the thromboplastin and the calcium salt are contained in separate tablets.

Thromboplastin is a phospholipid extracted from such organs as rabbit brain, human brain, monkey brain, rabbit lung, bovine brain, and ox brain. The thromboplastin may be extracted by the Quick Method as known in the art. A solution of the thromboplastin extract is formed by dissolving approximately 40–80 grams of the phospholipid material in one liter of saline. Preferably, the saline solution is 0.5% sodium chloride. The concentration of the saline may be from about 0.25% to about 0.85%. The activity of the phospholipid extract is determined by running a PT test as is well-known in the art. The results should be about 10 seconds to about 13 seconds with fresh normal citrated plasma.

A lyophilized reagent is formed by mixing phospholipid extract having a PT test activity as described above with a buffer, and preferably with an antimicrobial preservative, and a stabilizing agent. The preferred buffer is an imidazole/glycine mixture containing 0.05M imidazole and providing 2% by weight glycine, and having a pH of about 6.8 to 7.5. Other buffers such as tris(hydroxymethyl) aminomethane (referred to as tris), imidazole, barbitol, N-2-hydroxyethyl piperazine-N'-2-ethane sulfonic acid (referred to as HEPES), glycine and other buffers in the pH range of 6.8 to 7.5 may be used. Generally, from about 50 to about 75% by weight of such buffers is employed.

While any suitable antimicrobial preservative may be used, the preferred antimicrobial preservative is sodium azide. It is preferred to use 0.02% by weight of sodium azide; however, the concentration may vary from about 0.01% to about 0.3% by weight. Below about 0.01% the azide loses its effect and above about 0.3% by weight, there is no additional effect. Other preservatives such as sodium ethylmercurithiosalicylate (referred to as thimerosal), neomycin sulfate, phenol, or others known to inhibit microbial growth can also be used. Any suitable concentration of such preservatives to provide the desired preservative effect can be employed.

A stabilizing amount of any suitable stabilizer may be included in the thromboplastin-containing tablet. Preferably, the stabilizing agents are manganese chloride or magnesium chloride. The most preferred concentration of the stabilizing agent is about 0.01M, preferably from about 0.005M to about 0.02M.

For convenience, a half liter volume containing the buffer, and stabilizing agent and preservative, if desired, is added to one half liter of the thromboplastin extract A sample of the solution is taken and a PT test is run. The solution is adjusted to obtain a PT test result of about 10 seconds to about 13 seconds with fresh normal citrated plasma.

The thromboplastin manufacturing batch providing the above described PT test result is then lyophilized. The lyophilized reagent is then dry blended with a binder and lubricant.

Trehalose is a preferred binder. Another preferred binder is malto-dextrin such as AMAIZO LO-DEX 5 (a registered trademark of American Maize-Products Company) or Di-Pac (a registered trademark of Amstar Corporation). Di-Pac is made up of about 97% sucrose and about 3.0% malto-dextrin. Other binders such as sugars, celluloses, and starches may be used including sucrose, maltose, mannitol, lactose, acacia, gelatin, povidone, methylcellulose, carboxymethyl cellulose, hydrolyzed starch pastes and the like. Any amount of binder effective to provide the desired binding effect may be used. Generally, from about 0.5 to about 10% by weight of binder is used, preferably 3%, particularly 3% of trehalose. It is also preferred to add the binder, particularly trehalose, to the thromboplastin preparation before it is lyophilized.

A preferred lubricant is L-leucine. However any suitable binder known in the art may also be employed including, for example, polyethylene gylcol (PEG), magnesium stearate, glycine, silica such as Cab-O-Sil (a registered trademark of Cabot Corporation) and the like. Any lubricating amount of the lubricant may be employed; however, from about 1 to about 15% by weight is generally preferred, with about 5% by weight being most preferred.

It may be desirable to add a disintegrating agent such as starches, celluloses, or effervescent mixtures to the dry blend batch. Any suitable amount of such materials to produce the desired disintegrating effect may be employed and up to about 10% by weight is preferred.

The dry blend batch thus produced is tested by running a number of samples of the dry blend that average about 120 milligrams in weight in a PT time test. The results should yield a PT of 10 to 13 seconds using fresh normal citrated plasma. If the test results fall outside the 10 to 13 second range, the weight of the dry blend per tablet is proportionately adjusted to provide results within this range. Generally three samples are adequate to verify the test results.

The dry blend batch containing the thromboplastin can be combined with one or more dry blend batches that have been prepared and tested to form a final manufacturing batch larger than the amount that could be obtained from a batch lyophilizer. The same is true with respect to the dry blend batch containing the calcium. The advantage of a larger manufacturing batch and the tablets obtained therefrom is that the reagent may be used by a larger number of laboratories, thereby facilitating interlaboratory quality control comparisons.

The dry blend batches have a low bulk density and are not readily flowable. Therefore, the dry blended manufacturing batch is compacted to increase bulk density. The resultant compaction is granulated to make it flowable and minimize fines. The granules are screened to adjust the size of the granules used in the tableting process. The oversized granules may be further ground and the fines may be recompacted and regranulated.

Prior to tableting the granulated material, a sample is taken and another PT test is run to verify the amount of material by weight which should be used per tablet. If necessary, the size of the tablet is adjusted to yield a result of 10 to 13 seconds as previously described.

To prepare the calcium-containing tablet to be used with the thromboplastin microconcentrate, calcium lactate, calcium gluconate, or calcium chloride is dry blended with a lubricant and preferably also with a binder. Generally, it is important in a thromboplastin reagent of the type disclosed herein to introduce as few nonessential materials as possible and to use the smallest possible amounts. Therefore, while a bulking agent may be employed, the use of a bulking agent is not preferred. The amount of the calcium salt to be used per tablet is determined by the PT test. Generally about 0.0125M of calcium is used per sample in the test. The concentration of the calcium salts may vary from about 0.005M to about 0.02M, preferably from about 0.01M to about 0.02M, with the most preferred concentration being about 0.0125M.

Any suitable binder may be used, particularly as disclosed herein, including glycine, sucrose, maltose, mannitol, lactose, and other sugars; however, Di-Pac is preferred. Generally, from about 10% to about 80% by weight of the binder is employed, preferably about 30% to about 80% and most preferably about 40% by weight.

Any suitable lubricant may be used, particularly as disclosed herein, including PEG, magnesium stearate, talc, and the like; however, L-leucine is preferred. Generally, from about 3% to about 15% by weight of a lubricant is employed, preferably from about 5% to about 11%, and most preferably about 10%.

If desired, an effective amount of a disintegrating agent can be included in the tablet containing the calcium. Other materials that will not interfere with the reagent may also be included.

The dry blend batch containing calcium is tested by running samples of dry blend having an average weight of 120 milligrams in a PT test with a thromboplastin tablet as described herein. The results should be from about 10 seconds to about 13 seconds with fresh normal citrated plasma. If the test results fall outside the 10 to 13 second range, the weight of the dry blend per tablet is proportionately adjusted to provide results within this range. An adequate number of samples (for example 3-5) should be run to verify the results.

The dry blend batch, or two or more dry blend batches which have been combined to form a manufacturing batch and tested as described above, are compacted, granulated, screened, retested, and tableted as described above for the production of the thromboplastin-containing tablet.

The above described method may be modified by spraying a solution of lyophilized reagent and binder onto granules of the buffer. For convenience, about one liter of the buffer is lyophilized. If a stabilizing agent is to be included in the tablet, it is added to the buffer solution prior to lyophilization in the concentration and amounts previously disclosed.

Approximately 40 to 80% of the thromboplastin phospholipid are dissolved in one liter of 0.5% saline solution. About 3% by weight of the binder, preferably trehalose, is added to the thromboplastin/saline solution. This solution is then sprayed onto the granules of buffer and dried at about 2° to 8° C. under a high vacuum of at least about 300 microns for from about 8 to about 24 hours.

The concentration of the trehalose may be varied from about 0.5% to about 10% by weight. The amount of the buffer may be varied from about 50% to about 75% by weight as disclosed herein.

After the sprayed granules are dried, they are recompacted and regranulated. The lubricants described herein may be dry blended with the dry sprayed granules. However, it is preferred to add about 3% by weight of L-leucine, or other lubricant, after the regranulation and before tableting.

Alternatively, the method may be modified by spraying the buffer solution onto granules of lyophilized reagent and binder.

The tablets formed by the methods disclosed herein have substantial long term unreconstituted stability and short term reconstituted stability. The tablets are convenient to use and handle. Storage is facilitated by their small physical size. They dissolve readily, are easy to use, and provide uniform results.

The preparation of the coagulation reagents in tablet form reduces the packaging costs. Further, since the thromboplastin and calcium-containing tablets can be packaged in the same container or compartment without deleterious effect, there is no increase in packaging cost over the cost of packaging single tablet reagents.

Although the invention has been described in considerable detail in the foregoing, such detail is solely for the purpose of illustration. Variations can be made by those skilled in the art without departing from the spirit or scope of the invention, except as set forth in the claims.

What is claimed is:

1. An improved tableted microconcentrated blood plasma coagulation reagent which comprises a combination of a first tablet containing thromboplastin, a buffer, a binder, and a lubricant; and a second tablet containing a calcium salt selected from the group consisting of calcium lactate, calcium gluconate, and calcium chloride.

2. The improved tableted reagent of claim 1 wherein the second tablet also contains a binder and a lubricant.

3. The improved tableted reagent of claim 2 wherein the binder is selected from the group consisting of glycine, sucrose, maltose, mannitol, lactose, and a mixture of about 97% sucrose and about 3% malto-dextrin.

4. The improved tableted reagent of claim 3 wherein the binder is a mixture of about 97% sucrose with about 3% malto-dextrin.

5. The improved tableted reagent of claim 2 wherein the lubricant is selected from the group consisting of polyethylene glycol, magnesium stearate, talc, and L-leucine.

6. The improved tableted reagent of claim 5 wherein the lubricant is L-leucine.

7. The improved tableted reagent of claim 1 wherein the buffer is selected from the group consisting of imidazole, tris, HEPES, glycine and barbitol.

8. The improved tableted reagent of claim 7 wherein the buffer is an imidazole/glycine mixture containing 0.05M imidazole, 2% glycine and having a pH at 6.8 to 7.5.

9. The improved tableted reagent of claim 1 wherein the binder is selected from the group consisting of trehalose, malto-dextrin, sugars, celluloses, and starches.

10. The improved tableted reagent of claim 9 wherein the binder is 97% sucrose and 3% malto-dextrin.

11. The improved tableted reagent of claim 1 wherein the lubricant is selected from the group consisting of polyethylene glycol, magnesium stearate, talc, and L-leucine.

12. The improved tableted reagent of claim 11 wherein the lubricant is L-leucine.

13. The improved tableted reagent of claim 1 wherein the first tablet contains an antimicrobial preservative.

14. The improved tableted reagent of claim 13 wherein the preservative is sodium azide.

15. The improved tableted reagent of claim 1 wherein the first tablet contains a stabilizer selected from the group consisting of manganese chloride or magnesium chloride.

16. The improved tableted reagent of claim 1 wherein first tablet contains a disintegrating agent.

17. The improved tableted reagent of claim 1 wherein the first tablet contains from about 50 to 75% by weight of buffer, from about 0.5 to 10% by weight of binder, and from about 1 to 15% by weight of lubricant.

18. The improved tableted reagent of claim 17 containing up to about 10% by weight of a disintegrating agent.

19. The improved tableted reagent of claim 17 containing from about 0.01 to 0.3% by weight of an antimicrobial preservative.

20. The improved tableted reagent of claim 17 containing from 0.005 to 0.02M of a stabilizer selected from the group consisting of manganese chloride or magnesium chloride.

21. The improved tableted reagent of claim 2 wherein the second tablet contains from about 15 to 85% by weight of calcium salt, from about 10 to 80% by weight of binder, and about 3 to 15% by weight of lubricant.

* * * * *